(12) United States Patent
McGhan

(10) Patent No.: US 6,913,626 B2
(45) Date of Patent: Jul. 5, 2005

(54) MEDICAL IMPLANT HAVING BIOABSORBABLE TEXTURED SURFACE

(76) Inventor: Jim J. McGhan, 1865 Meiners Rd., Ojai, CA (US) 93023

( * ) Notice: Subject to any disclaimer, the term of this patent is extended or adjusted under 35 U.S.C. 154(b) by 0 days.

(21) Appl. No.: 09/931,692

(22) Filed: Aug. 14, 2001

(65) Prior Publication Data

US 2003/0036803 A1 Feb. 20, 2003

(51) Int. Cl.$^7$ ................................................ A61F 2/02
(52) U.S. Cl. ................ 623/23.73; 623/8; 623/23.72; 623/23.74; 623/23.75; 623/11.11
(58) Field of Search ............................. 623/7, 8, 11.11, 623/23.58, 23.72–23.76, 1.1, 1.38, 1.39, 1.42–1.47, 23.59

(56) References Cited

U.S. PATENT DOCUMENTS

| | | | |
|---|---|---|---|
| 3,852,832 A | * 12/1974 | McGhan et al. ............... 3/36 |
| 4,298,998 A | * 11/1981 | Naficy ........................... 3/36 |
| 4,889,744 A | * 12/1989 | Quaid ............................ 427/2 |
| 4,955,909 A | *  9/1990 | Ersek et al. .................. 623/11 |
| 5,197,977 A | *  3/1993 | Hoffman, Jr. et al. ......... 623/1 |
| 5,383,927 A | *  1/1995 | De Goicoechea et al. ..... 623/1 |
| 5,525,275 A | *  6/1996 | Iversen et al. ............... 264/28 |
| 5,964,803 A | * 10/1999 | Iversen et al. ............... 623/8 |
| 6,017,366 A | *  1/2000 | Berman ....................... 623/21 |
| 6,071,305 A | *  6/2000 | Brown et al. .................. 623/1 |
| 6,143,037 A | * 11/2000 | Goldstein et al. ............ 623/65 |
| 6,214,045 B1 | *  4/2001 | Corbitt, Jr. et al. ........... 623/8 |
| 6,299,930 B1 | * 10/2001 | Marotta et al. ............ 427/2.28 |
| 6,413,539 B1 | *  7/2002 | Shalaby ...................... 424/426 |
| 6,497,729 B1 | * 12/2002 | Moussy et al. .......... 623/23.57 |
| 6,506,437 B1 | *  1/2003 | Harish et al. ............. 427/2.25 |
| 6,599,323 B2 | *  7/2003 | Melican et al. .......... 623/23.72 |
| 2002/0052653 A1 | * 5/2002 | Durgin |

\* cited by examiner

*Primary Examiner*—Bruce Snow
*Assistant Examiner*—Cheryl Miller
(74) *Attorney, Agent, or Firm*—Michael G. Petit

(57) ABSTRACT

A hybrid medical implant having a biocompatible, nonabsorbable core portion and a bioabsorbable textured outer surface portion overlying the core portion. The hybrid implant is useful as a prosthesis for tissue augmentation and/or reconstruction. The core portion of the implant includes a body formed from a nonabsorbable, biocompatible implantable material such as silicone or urethane elastomer. The core portion may be either a solid body, a viscous gel body or a fluid-filled shell. The textured outer surface portion envelops the core portion and presents an irregular, bioabsorbable textured surface to the exterior environment. As a capsule forms around the implant following implantation, the irregular contour of the outer surface of the implant disorients structural proteins in the capsule to impede spherical contraction thereof. Either during the formation of the capsule and/or after the capsule is formed, the outer bioabsorbable surface portion of the implant is absorbed by the body of the host. After bioabsorbtion of the bioabsorbable outer surface portion, the remaining core portion of the implant remains enveloped by the capsule but unattached to capsular tissue. The outer bioabsorbable portion of the hybrid implant may include more than one biocompatible, bioabsorbable material.

5 Claims, 3 Drawing Sheets

MEDICAL IMPLANT HAVING BIOABSORBABLE TEXTURED SURFACE

BACKGROUND OF THE INVENTION

1. Field of the Invention

The invention relates to medical implants and more particularly to implantable prostheses.

2. Prior Art

Medically implantable prostheses, exemplified by breast implants, are well known in the art. Such implants generally comprise a formed body presenting a nonreactive, biocompatible outer surface to surrounding tissue following implantation. The implant is recognized as a foreign body by the host's immune system and is encapsulated, walling the implant off from the rest of the host's body. As the capsule ages, molecular rearrangement within the capsule change the overall shape of the capsule. If the implant is deformable, such as is the case with fluid-filled prostheses, the shape of the implant will change to conform to the shape of the surrounding capsule. In many patients hosting fluid-filled prostheses, such as patients receiving a breast implant, the capsule slowly undergoes "spherical contracture", palpably changing the shape and feel of the implant. Such spherical contracture is generally regarded as undesirable.

Fluid-filled medical implants generally comprise a viscous fluid contained within an elastomeric shell. It has been observed that fluid-filled medical implants presenting a smooth outer surface to surrounding tissue are particularly susceptible to deformation due to capsular contracture. In order to overcome, or at least minimize, the effect of capsular contracture, fluid-filled medical implants have been developed that have a textured outer surface. The irregular topography of the outer surface apparently induces molecular disorganization in the capsule that forms around the implant following implantation. Such molecular disorganization in the capsule is believed to resist spherical contracture.

In order to texture the outer surface of implants, two methods are commonly used in the art. In a first method, described by Quaid in U.S. Pat. No. 4,889,744, a layer comprising a biocompatible, nonbioabsorbable uncured silicone elastomer is applied to the outer surface of a silicone implant. Before the layer is permitted to cure, solute particles, usually salt, are embedded in the (tacky) outer layer. The outer layer bearing the solute particles is then partially cured and exposed to an appropriate solvent to remove the solute particles. The outer layer is then fully cured. The plurality of voids remaining in the layer following removal of solute and curing have an open celled structure. The resulting medical implant has both a textured outer surface and unitary construction. An alternative embodiment of the first method comprises the formation of outwardly projecting fibrils on the outer surface. Again, the fibrils comprise a nonbioabsorbable material.

In a second method, as disclosed by Brauman in U.S. Pat. No. 4,648,880 and RE35,391, an implantable prosthesis comprises a flexible container with a soft gel or fluid filling and an outer plastic or polymeric covering bonded to, and substantially enveloping the flexible container. The outer plastic polymeric covering is made from a woven mesh fabric such as Dacron® (poly(ethylene glycol terephthalate)) or Teflon®, and has numerous pores or interstices within the material as well as a rough textured external surface. The outer plastic covering, comprising a nonbioabsorbable mesh, such as woven Dacron® fabric, is glued to the outer surface of the implant to provide a rough textured outer surface. While this type of implant provides a textured outer surface that is functionally similar to implants made by the first method, the implant lacks unitary construction which can lead to structural failure, such as delamination, following implantation within the body.

Either of the foregoing prior art texturing methods have advantages and disadvantages. While both methods appear to provide an implant that resists capsular contracture, the second method provides an outer layer that may delaminate within the body. For this reason, the first method of making an implant having a textured outer surface is currently favored over the second method. In the first method, the outer tissue contacting surface of the implant provides means for disrupting and/or disorganizing the orderly alignment of the structural proteinaceous biopolymers comprising the capsule during capsule formation. The outer surface, when textured in accordance with the first method, also permits capsular tissue to grow into the plurality of (open celled) interstices in the outer surface of the implant. The partial or total adhesion of the implant to the capsule due to such tissue ingrowth may be undesirable in the event it becomes necessary to remove or replace the implant. Further, partial or asymmetric adhesion between the capsule and the outer surface of the implant may give rise to undesirable cosmetic effects. Notwithstanding the foregoing disadvantages, textured implants having a biocompatible, nonbioabsorbable outer tissue-contacting surface are generally considered to reduce the incidence of capsular contracture in patients. There remains a need for an implantable fluid-filled prosthesis that resists capsular contracture following implantation and that resists adherence of the implant to the capsule.

SUMMARY

The present invention discloses a medical implant that has a textured outer tissue contacting surface and resists tissue ingrowth. The medical implant is a hybrid structure comprising a nonbioabsorbable elastomeric core portion and a bioabsorbable outer surface portion. The bioabsorbable outer surface portion of the implant is topographically varied, providing interstices for capsular tissue ingrowth. The outer surface portion is bioabsorbed by the body preferably 3–12 months following implantation. The time required for bioabsorbtion of the outer surface portion can be varied by the choice of bioabsorbable material used to form the outer surface portion.

It is, therefore, a primary object of the invention to provide a medical implant that, when implanted within the body of a host, resists deformation due to capsular contracture and does not adhere to the capsule after the capsule is formed.

The features of the invention believed to be novel are set forth with particularity in the appended claims. However the invention itself, both as to organization and method of operation, together with further objects and advantages thereof, may be best understood by reference to the following description taken in conjunction with the accompanying drawings in which:

DESCRIPTION OF THE PREFERRED EMBODIMENTS

Figure 1:
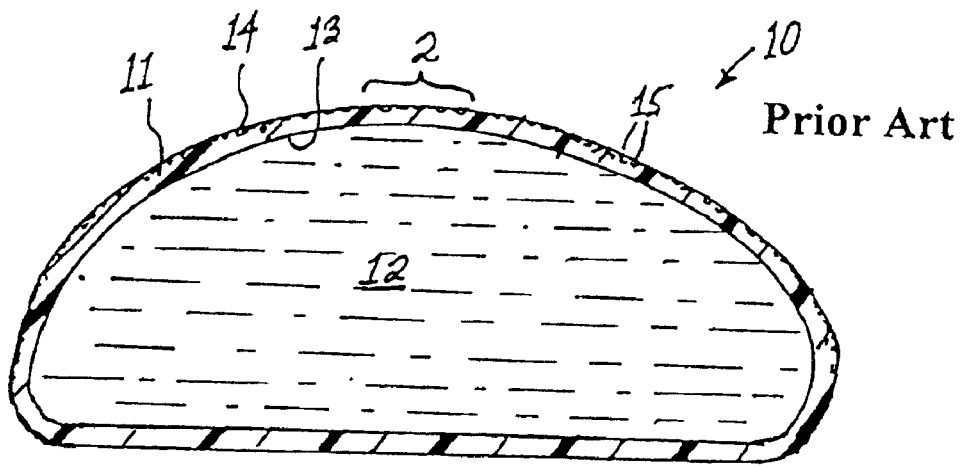
FIG. 1 is a cross-sectional view of a fluid-filled implant having a textured outer surface in accordance with the prior art.
Figure 2:
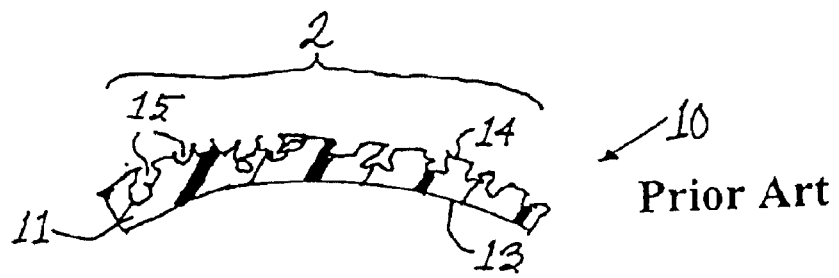
FIG. 2 is an enlarged cross-sectional view of the portion of the implant indicated at numeral 2 in FIG. 1.

With reference to FIG. 1, a medical implant in accordance with the prior art is shown in cross-sectional view at numeral 10. The implant 10 comprises a (normally extensible) silicone shell 11 containing a fluid 12 such as saline or silicone gel. The elastomeric shell 11 has an inner surface 13 and an outer surface 14. The outer surface 14 of the shell 11 is characterized by a plurality of pores 15 disposed in the outermost portion of the shell 11. The pores 15, which are shown in greater detail in FIG. 2, are dimensioned to permit the passage of fibroblasts thereinto. The pores 15, in accordance with textured outer surfaces 14 on many prior art implants, are preferably in the range of 0.1–0.5 mm in diameter and open celled in structure. The size of the pores is important because capsular ingrowth requires the migration of fibroblast cells into the pores to facilitate deposition of connective tissue within the pores. Such connective tissue, deposited within the pores, is integral with and part of the structure of the capsule. It is believed that the irregular topography of the outer surface 14 of the implant induces disorganization in the adjacent collagen layers comprising the surrounding capsule, which disorganization, in turn, extends into collagen layers throughout the capsule thereby inhibiting capsular contracture. The capsule 51 (shown in FIG. 5) thus formed is adhered to the implant via fibrous tendrils 52 extending into the pores. The term "irregular topography", as used herein to describe a surface, means that the surface is textured, having a plurality of pits therein and/or a plurality of peaks projecting outwardly therefrom.

Before proceding further, it is instructive to review how fluid-filled implants such as the example shown at 10 in FIG. 1 are made. Fluid-filled implants 10, having a formed shell 11, are normally made by the repetitive dipping of a shaped mandrel into a dispersion of an appropriate (biocompatible, nonbioabsorbable) elastomer. During the dipping process, the outermost, or most recent layer of elastomer dispersion coating deposited on the mandrel (and any previously deposited undercoats therebetween) is cured between sequential dips. In this manner, the shell is gradually built up like an onion to the required thickness. The thickness of each concentric layer comprising the shell can be varied by changing the viscosity of the dispersion.

Figure 3:
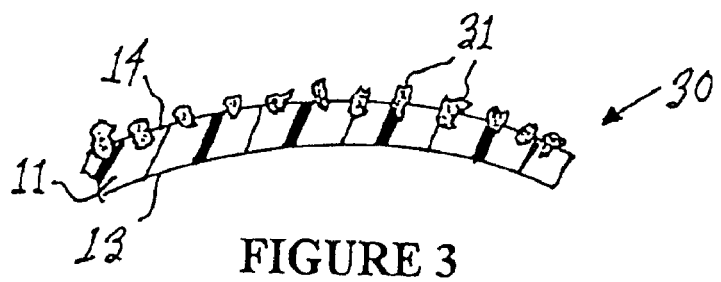
FIG. 3 is a cross-sectional view of a portion of a first preferred embodiment of an implant in accordance with the present invention.
Figure 6:
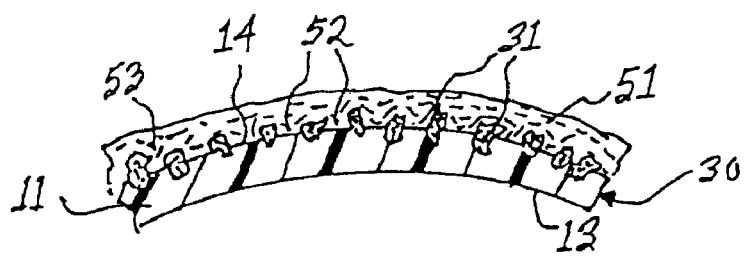
FIG. 6 is a cross-sectional view of the first preferred embodiment of an implant in accordance with FIG. 3, and following implantation within the body, showing the fibrous capsule forming therearound.

Turning now to FIG. 3, a first embodiment of an implant in accordance with the present invention is shown in partial cross-sectional view at numeral 30. The shell 11 comprises a nonbioabsorbable, biocompatible elastomer such as silicone having a plurality of bioabsorbable particles 31 affixed to the outer surface thereof. The bioabsorbable particles 31, which may be irregularly shaped, have a least dimension that is greater than the thickness of the outermost layer of elastomer; preferably in the range of 0.1–0.5 mm, and a greatest dimension preferably in the range 0.2–1.0 mm. The plurality of bioabsorbable particles 31 may be applied to the final, outermost coating of elastomer dispersion prior to curing on the mandrel. When the outermost layer of dispersion is cured, the plurality of bioabsorbable particles is partially embedded therein and affixed thereto. The least dimension of the bioabsorbable particles 31 is selected to be greater than the thickness of the outermost layer of dispersion in order to assure that a portion of each of the particles 31 will project outwardly from the elastomeric shell and present an irregular topography having a plurality of tortuous channels or recesses between the exposed portion of the particles into which capsular tissue can grow, as shown in FIG. 6. For example, if the thickness of the outermost layer of elastomer dispersion is 10 mil (0.25 mm), the least dimension of the particles must be greater than 0.25 mm, and preferably about 0.5 mm. Such bioabsorbable particles will then have a portion that projects outwardly at least 0.25 mm beyond the surface of the outermost cured layer of elastomer, presenting a rough, textured and topographically varied surface to surrounding tissue after implantation.

Figure 5:
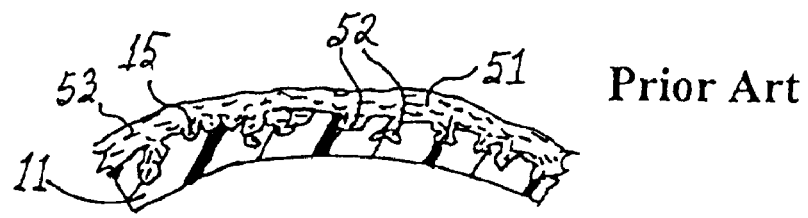
FIG. 5 is a cross-sectional view of the first preferred embodiment of an implant in accordance with FIG. 2, and following implantation within the body, showing the fibrous capsule forming therearound.

When a prior art implant 10 is implanted beneath the skin of a person, a capsule 51 comprising connective tissue begins to form around the implant as shown in partial cross-sectional view in FIG. 5. The capsule 51 is tough and fibrous; having the general appearance of scar tissue. The chains of structural biopolymers 53 comprising the capsule are crosslinked to one another to provide organization and structural integrity to the capsule. During capsule genesis, fibrils 52, threadlike portions of the capsule, penetrate the pores 15 comprising the outer surface of the implant. The discontinuity in the contour of the capsule prevents optimal alignment between adjacent biopolymers which is thought to reduce capsular contracture. In addition, the ingrowth of the fibrils 52 within the implant affixes the implant to the capsule. In some instances, such connection may be desirable. In others, it may be disadvantageous. Since the outer surface of the implant 10 is not bioabsorbable, the capsule remaining adhered to the implant many years after implantation.

Figure 7:
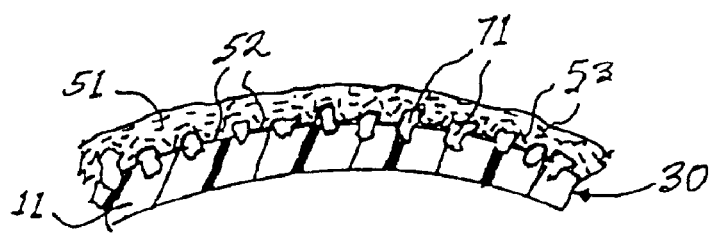
FIG. 7 is a cross-sectional view of the first preferred embodiment of an implant in accordance with FIG. 6, showing the fibrous capsule formed therearound and with the bioabsorbable particles embedded in the outer layer absorbed by the body.

In contrast, and as shown in FIG. 6, when an implant 30 in accordance with the first embodiment of the present invention is implanted beneath the skin of a patient, the presence of the implant triggers the body's inflammatory response and a capsule 51 forms as described above. The tendrils 52, however, project inwardly from the capsule to penetrate the channels between the bioabsorbable particles 31. After the capsule has formed, the bioabsorbable particles 31 disintegrate due to hydrolysis and/or other biodegradative mechanisms and the capsule 51 and implant 30 are no longer attached. After the degradation and bioabsorbtion of the bioabsorbable particles is complete, a plurality of voids 71 occupy the space previously occupied by the plurality of bioabsorbable particles 31, as illustrated in FIG. 7.

Figure 4:
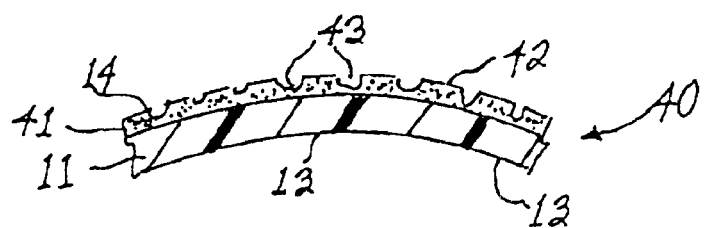
FIG. 4 is a cross-sectional view of a portion of a second preferred embodiment of an implant in accordance with the present invention.

FIG. 4 is a cross-sectional view of a portion of a second preferred embodiment of an implant in accordance with the present invention. The implant 40 comprises a nonbiodegradable, biocompatible elastomeric shell 11 having a bioabsorbable outer layer 41 bonded to the outer surface 14 thereof. The bioabsorbable outer layer 41 is topographically irregular on the outermost surface 42 thereof. The topographical irregularity on the outermost surface 42 of the bioabsorbable outer layer 41 may be achieved by forming a plurality of depressions or craters 43 therein, as illustrated in FIG. 4, or the bioabsorbable outer layer 41 may have a porous or open celled structure.

Figure 8:
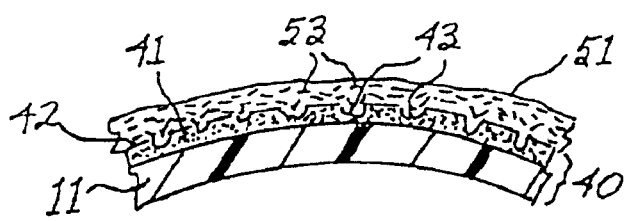
FIG. 8 is a cross-sectional view of the second preferred embodiment of an implant in accordance with FIG. 4, and following implantation within the body, showing the fibrous capsule forming therearound.
Figure 9:
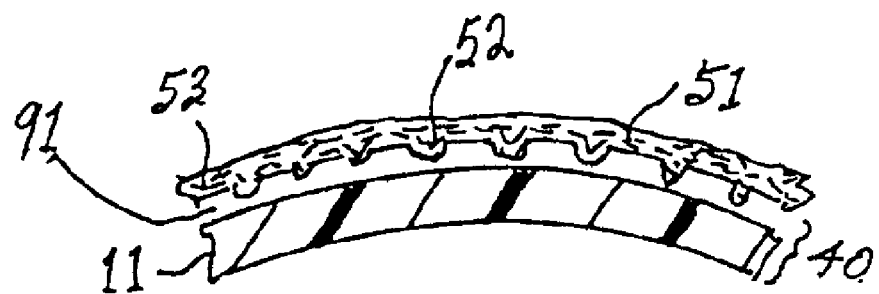
FIG. 9 is a cross-sectional view of the second preferred embodiment of an implant in accordance with FIG. 8, showing the fibrous capsule formed therearound and with the bioabsorbable outer layer absorbed by the body.

FIG. 8 is a cross-sectional view of the second preferred embodiment of an implant 40, illustrated in FIG. 4, after it has been implanted within the body of a patient, showing the fibrous capsule 51 forming therearound. Again, the structural biopolymers 53 comprising the capsule 51 are disoriented by the irregular topography of the outer surface of the bioabsorbable outer layer 41 of the implant 40. However, following implantation and capsule formation, the bioabsorbable outer layer is absorbed by the body to leave a void 91 between the shell 11 and the capsule 51. The inwardly projecting capsular fibrils 52 are not adhered to the implant yet the implant is encased by the capsule.

In the embodiments of a hybrid implant in accordance with the present invention, the choice of biodegradable material must be such that the structural integrity of the bioabsorbable portion of the implant is retained for 2–3 months following implantation in order to allow sufficient time for the capsule to form. There are many materials that may be used to form a bioabsorbable outer layer. For example, the outer layer may comprise a bioabsorbable material selected from the group comprising polymers or copolymers of lactide, glycolide, caprolactone, polydioxanone, trimethylene carbonate, polyorthoesters and polyethylene oxide. McGregor et al., in U.S. Pat. No. 5,869,080, discloses a porous collagen and a method for making the collagen that may prove suitable as a bioabsorbable outer portion of implants of the present invention. In addition to the forgoing bioabsorbable, non-toxic materials, high molecular weight polysaccharides from connective tissue such as chondroitin salts may be employed for the purpose of practicing the invention. Other polysaccharides may also prove suitable, such as chitin and chitosan. Additional bioabsorbable materials are in intense development and it is expected that many of the new materials will also be applicable for forming a textured bioabsorbable outer layer on a medical implant.

A number of processes are known for preparing finely divided polymeric particles, e.g., mechanical grinding, solvent precipitation, dispersion, spray atomization of solutions or slurries and rotary atomization. In rotary atomization, the polymer is applied to a rotating bell, cup, or disk, with mechanical forces predominating in the breakup of the polymer into particles. More specifically, the polymer is introduced near the center of the rotating bell, cup, or disk whereby centrifugal force distributes the polymer to the edge of the rotating bell, cup, or disk, at which the polymer has an angular velocity close to the angular velocity of the rotating bell, cup, or disk. As the polymer leaves the surface of the rotating bell, cup, or disk at the outer edge thereof, a principal velocity component thereof is tangential to the rotating member, and the polymer is spun off in the form of a thin sheet or small cusps. The flowable polymer is then atomized by turbulent or aerodynamic disintegration, depending upon conditions. Generally, viscosity of the polymer being atomized is as low as possible to enhance atomization. U.S. Pat. No. 3,743,464 discloses an apparatus for sphering small particles which comprises a plurality of concentric, radially-spaced cylinders and a rotating plate underneath, with material introduced into the innermost cylinder being gradually sphered and propelled through openings into adjacent outer cylinders. U.S. Pat. No. 3,741,703 relates to improving uniformity of particle size generated during rotary atomization by turning upwardly the peripheral edge of the rotating atomization plate, whereby the particles of material broken up on the atomization plate are subjected to a more uniform flow and even treatment.

Chesterfield et al., in U.S. Pat. No. 5,143,662, disclose a method for producing particles of bioabsorbable polymer which comprises subjecting the bioabsorbable polymer, having a viscosity of at least about 0.28 cp., to rotary atomization employing a rotary atomization unit possessing a substantially circular rotating element upon whose surface the polymer is made to impinge. Upon impact, the polymer breaks up into particles which are thrust away from the rotating element to solidify in free flight, the conditions of rotary atomization providing solid particles of the polymer within a range of average particle size of from about 0.1 to about 3 mm., and including a polymer temperature of from about 200 degrees C. to about 300 degree C., a rate of rotation of the rotating element of from about 100 to about 1,000 rpm., and a temperature of the rotating element of from about 200 degrees C. to about 300 degrees C. Thus, since many of the above-listed bioabsorbable polymers have a melting point below 300 degrees C., this method may be used to make a variety of bioabsorbable polymers with different absorbtion rates ranging from days to many months, depending on the particular polymer.

The method for affixing the bioabsorbable outer layer to the nonbioabsorbable portion of the implant, as well as the method for establishing a topographically irregular method may be used to make a variety of bioabsorbable polymers with different absorbtion rates ranging from days to many months, depending on the particular polymer.

The method for affixing the bioabsorbable outer layer to the nonbioabsorbable portion of the implant, as well as the method for establishing a topographically irregular outer surface on the bioabsorbable portion of the implant, varies in accordance with the chemical and physical properties of the selected bioabsorbable material. At the present time, silicone is a preferred material for making the nonbioabsorbable portion of a medical implant, such as the shell 11 for a fluid-filled implant described above, commonly used for making prostheses for soft tissue replacement or augmentation. The hydrophobicity of silicone presents an adhesion problem for hydrophilic bioabsorbable materials that may require coating one or both surfaces (i.e., both the bioabsorbable particles and the silicone substrate) prior to adhesion. A preferred method for adhering most bioabsorbable particulates to the outer surface of a nonbioabsorbable material is to apply a coat of silicone dispersion thereto and press or otherwise force a portion of the bioabsorbable particles into the layer of dispersion while the layer is still tacky, then curing the outer coating of dispersion.

It will be recalled that it is a primary purpose of the present invention to provide an implant that controls the organization and orientation of structural proteins in the capsule during capsule genesis following implantation of the implant within a host and resists adhesion between the implant and the surrounding capsule. The embodiments discussed above accomplish this by temporarily presenting a topographically irregular, bioabsorbable textured outer surface contour to the surrounding tissue. The persistence of the structural integrity of the bioabsorbable portion of the implant within a host is sufficient to disrupt organization of structural protein within the capsule during capsule formation.

In yet another embodiment of the invention, an implant is disclosed comprising a nonbioabsorbable core portion having a plurality of bioabsorbable materials disposed on the outer surface of the core portion. Each of the different bioabsorbable materials is selected to have a rate of bioabsorbtion within the body that is different from the rate of bioabsorbtion of the other bioabsorbable materials selected to comprise the bioabsorbable portion of the implant. Such a hybrid implant presents an irregular and changing topographic surface contour to the surrounding tissue after implantation therewithin. Such a hybrid implant is illustrated in FIG. 10.

Figure 10:
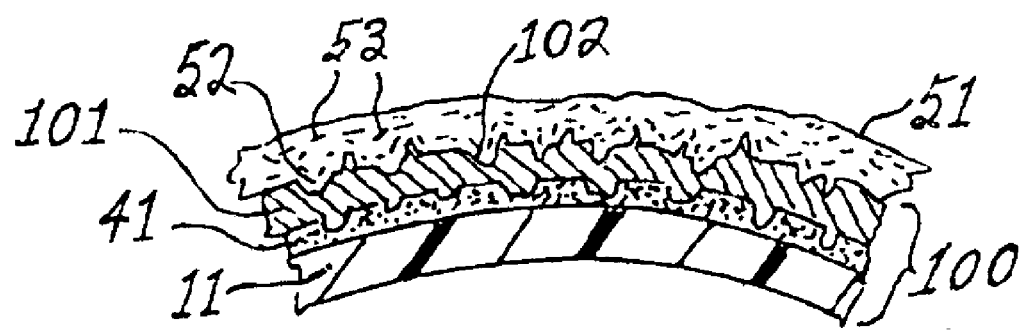
FIG. 10 is a cross-sectional view of a third preferred embodiment of a outer portion of a hybrid implant in accordance with the present invention wherein the outer bioabsorbable portion of the implant comprises two different bioabsorbable materials having different rates of biodegradation following implantation within a host organism.

FIG. 10 is a cross-sectional view of a third preferred embodiment of a outer portion of a hybrid implant 100 in accordance with the present invention wherein the outer bioabsorbable portion of the implant comprises two different bioabsorbable materials 41 and 101 having different rates of biodegradation following implantation within a host organism. The outermost surface of bioabsorbable material 101 is textured to provide a topographically irregular surface contour to the implant 100. As the capsule 51 forms around the implant 100, discontinuities 102 in the surface contour of the outer surface of the implant 100 disorient structural proteins 53 within the capsule. As the bioabsorbable material 101 disintegrates over time, the second, innermost bioabsorbable layer 41 is exposed, presenting a different contour to the surrounding capsular tissue. Upon continued exposure to the autogenous body fluids of the host, the innermost layer of bioabsorbable material 41 disintegrates, being either metabolized or excreted by the host organism. The space occupied by the bioabsorbable portion of the implant 100, comprised of bioabsorbable materials 41 and 101, is eventually replaced with autogenous body fluids; the implanted core portion 11 remaining free of adhesion to the surrounding capsule 51. In addition, one or more of the bioabsorbable materials comprising the bioabsorbable portion of the implants disclosed herein may include an antibiotic that is released by the bioabsorbable material either before or during biodegradation of the bioabsorbable material.

While particular embodiments of the present invention have been illustrated and described, it would be obvious to those skilled in the art that various other changes and modifications can be made without departing from the spirit and scope of the invention. For example, the outer bioabsorbable portion of the hybrid implant may comprise powders, spheres, crystals, coatings or any other physical form of a biocompatible, bioabsorbable material. The rate of degradation of the bioabsorbable material(s) comprising the implant may range between ten percent by weight per day to ten percent by weight per month or even ten percent by weight per year. Thus, it is therefore intended to cover in the appended claims all such changes and modifications that are within the scope of this invention.

What I claim is:

1. A hybrid medical implant comprising an elastomeric, nonbioabsorbable core portion having an outer surface and a plurality of discrete particles of a bioabsorbable material partially embedded in said outer surface such that an exposed portion of said particles projects outwardly from said outer surface, said exposed portion of said particles and said outer surface of said core portion in combination providing an outer surface of said hybrid medical implant and wherein said outer surface of said hybrid medical implant has an irregular topography such that immediately upon implantation of the hybrid medical implant within the body, the exposed portion of said plurality of particles of bioabsorbable material project outwardly from said outer surface of said core portion; and after the particles of bioabsorbable material are absorbed by the body, the outer surface of said core portion of said hybrid medical implant has a plurality of open craters therewithin, said hybrid medical implant being made by a process including the steps of: (a) coating an outer surface of an implantable article with a curable elastomeric composition to form an uncured core portion; then (b) applying a plurality of discrete bioabsorbable particles to said uncured core portion such that said bioabsorbable particles are only partially embedded within said uncured core portion; then (c) curing said uncured core portion.

2. The hybrid medical implant of claim 1 wherein said core portion comprises a fluid-filled elastomeric shell.

3. The hybrid medical implant of claim 1 wherein said core portion comprises a solid elastomeric body.

4. The hybrid medical implant of claim 1 wherein said elastomeric core portion comprises silicone.

5. A hybrid medical implant of claim 1 wherein said bioabsorbable particles comprises an antibiotic.

* * * * *